US006780161B2

United States Patent
Faragalla et al.

(10) Patent No.: US 6,780,161 B2
(45) Date of Patent: Aug. 24, 2004

(54) APPARATUS FOR EXTRACORPOREAL SHOCK WAVE LITHOTRIPTER USING AT LEAST TWO SHOCK WAVE PULSES

(75) Inventors: Yousry Faragalla, Lorton, VA (US); Alaa M. Elsheikh, Lorton, VA (US); Wadie G. Shehata, Lorton, VA (US)

(73) Assignee: FMD, LLC, Lorton, VA (US)

( * ) Notice: Subject to any disclaimer, the term of this patent is extended or adjusted under 35 U.S.C. 154(b) by 111 days.

(21) Appl. No.: 10/102,640

(22) Filed: Mar. 22, 2002

(65) Prior Publication Data

US 2003/0181833 A1 Sep. 25, 2003

(51) Int. Cl.$^7$ ................................. A61B 1/00
(52) U.S. Cl. .................. 601/2; 601/1; 601/3; 600/439; 604/22; 310/22
(58) Field of Search ............................. 601/2; 604/22; 310/22; 600/439

(56) References Cited

U.S. PATENT DOCUMENTS

| | | | |
|---|---|---|---|
| 3,942,531 A | | 3/1976 | Hoff et al. |
| 4,957,099 A | * | 9/1990 | Hassler .......................... 601/4 |
| 5,178,135 A | * | 1/1993 | Uchiyama et al. ............. 601/4 |
| 5,209,221 A | | 5/1993 | Riedlinger et al. |
| 5,219,401 A | | 6/1993 | Cathignol et al. |
| 5,358,466 A | * | 10/1994 | Aida et al. ....................... 601/4 |
| 5,374,236 A | * | 12/1994 | Hassler .......................... 601/2 |
| 5,381,792 A | * | 1/1995 | Yanagida et al. ........... 600/439 |
| 5,431,621 A | * | 7/1995 | Dory ............................. 601/2 |
| 5,501,655 A | * | 3/1996 | Rolt et al. ...................... 601/3 |
| 5,582,578 A | | 12/1996 | Zhong et al. |
| 6,123,679 A | | 9/2000 | Lafaut et al. |
| 6,254,553 B1 | * | 7/2001 | Lidgren et al. ................ 601/3 |
| 6,595,934 B1 | * | 7/2003 | Hissong et al. ................ 601/3 |

OTHER PUBLICATIONS

Chaussy et al., Extracorporeal Shockwave Lithotripsy 1982 edition, ISBN 3–8055–3620–2, pp. 5–6.
Eisenberger et al., Stone therapy in Urology, 1991 edition, ISBN 3–13713–3017, pp. 30–32.

* cited by examiner

Primary Examiner—Angela D. Sykes
Assistant Examiner—William C. Jung
(74) Attorney, Agent, or Firm—Jim Zegeer

(57) ABSTRACT

The present invention relates to an apparatus for treating a living body or tissue with shock waves originating from at least two sources to a focal area on or within said living body or tissue. The apparatus is particularly for treating an illness or fragmenting stones or concretions. The sources of shock waves are at different angles from one another. An objective of the invention is to induce a localized effective shock wave treatment area and at the same time to minimize or abolish the unwanted tissue damage effects outside the treatment area.

6 Claims, 3 Drawing Sheets

APPARATUS FOR EXTRACORPOREAL SHOCK WAVE LITHOTRIPTER USING AT LEAST TWO SHOCK WAVE PULSES

FIELD OF INVENTION

The invention relates to an apparatus for improving the efficiency of shock waves treatment in a living body or tissue while, at the same time, reducing the harmful effects of such treatment and to a method of treating a living body or tissue with such an apparatus.

BACKGROUND OF THE INVENTION

In the past two decades fragmentation of concretions inside a living body by focused shock wave from outside the body was established as a method of treatment. Recent research is also developing for the application of shock wave treatment in the field of Orthopedics and in pathological tissue ablation as well as in other different types of treatment.

The mechanisms by which focused shock waves disintegrates stones in Extracorporeal Shock Wave Lithotripsy are still not well understood. However several mechanisms for stone fragmentation have been proposed and documented in the literature.

The shock wave pulse comprises of a positive peak pressure up to about 120 Mpa, which lasts for up to about 2 microseconds followed by negative peak pressure up to about 20 MPa with about 2 to 8 microseconds duration.

It is further known in the art that the negative pressure induces transient cavitation bubbles around the focal point. Ensuing pulses cause these cavitation bubbles to collapse. When bubbles collapse adjacent to a solid surface like a stone it will take place asymmetrically leading to the formation of high speed, liquid micro jets that hit the stone surface and cause cracking and fragmentation.

Only a percentage of this micro jets, is directed to the stone while the remaining part, is consumed by the adjacent tissues leading to tissue damage.

It is also mentioned in the literature that the conditions required for fracturing stones include one or more of the following; compression and release, tension or spall and cavitation induced stress. Fragmentation involves separation of crystal layers and fracture and cleavage of crystals. The disintegration of stones occurs by the progressive initiation of cracks and their stepwise extension through the material. Brittle materials fail under compressive shock loading by initiation and growth of micro cracks from internal defects such as pores or inclusion or from material boundaries such as interfaces with organic or fibrous material or grain boundaries.

With repeated pulses the micro cracks grow on a prospective spall plane and they coalesce on reaching a critical length creating a fragment. Under pressure, the micro cracks grow in the axial plane; i.e. the failure is in the direction of maximum applied compression that is the direction of shock wave propagation. On the other hand, under tension micro cracks grow on a plane perpendicular to the direction of applied tension i.e. perpendicular to the direction of the shock wave propagation.

SUMMARY OF THE INVENTION

The present invention is based upon the discovery that the collapse of the cavitation bubbles can be controlled by the timing and direction of additional shock waves. Hence the use of one or more other shock wave sources to generate another shock wave propagating at an appropriate angle from the direction of propagation of the primary shock wave will enhance the treatment effect of shockwave and would abolish or minimize the tissue damage out side the focal area. The value of the angle between these shock wave sources varies according to various factors such as the type of treatment and the level of energy. The timing of generation of shock waves from these sources could be instantaneous or with a delay period between each of up to about 100 millisecond. This delay varies according to various factors such as the type of treatment and level of energy.

BRIEF DESCRIPTION OF THE DRAWINGS

To enable a better understanding of the present invention, the drawings illustrate a preferred embodiment of the invention.

DETAILED DESCRIPTION OF THE PREFERRED EMBODIMENT

Figure 1:
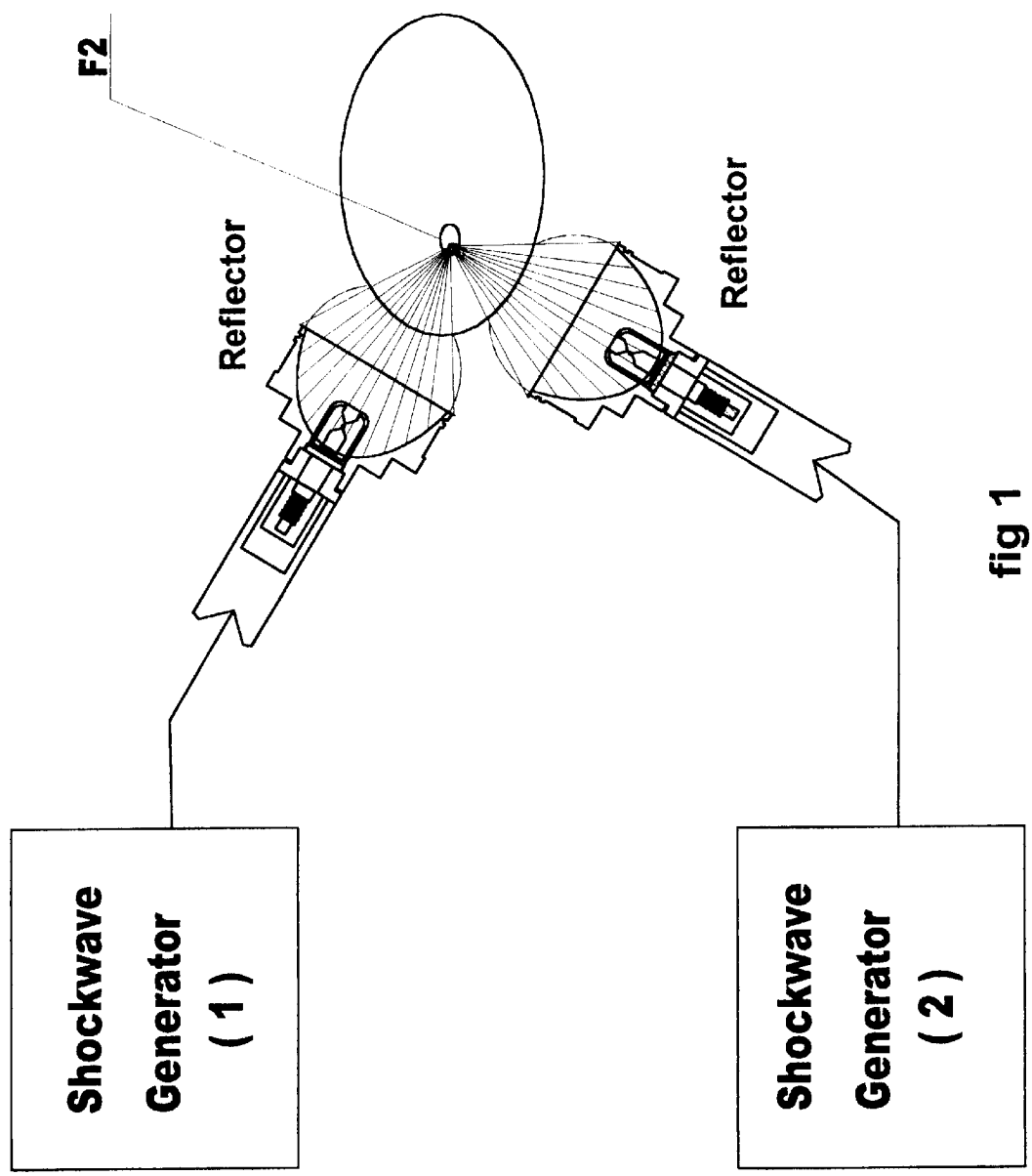
FIG. 1 is a schematic drawing that shows two shock wave generators connected to two reflectors, which are focusing the two shock waves to a focal point F2 inside the living body.
Figure 2:
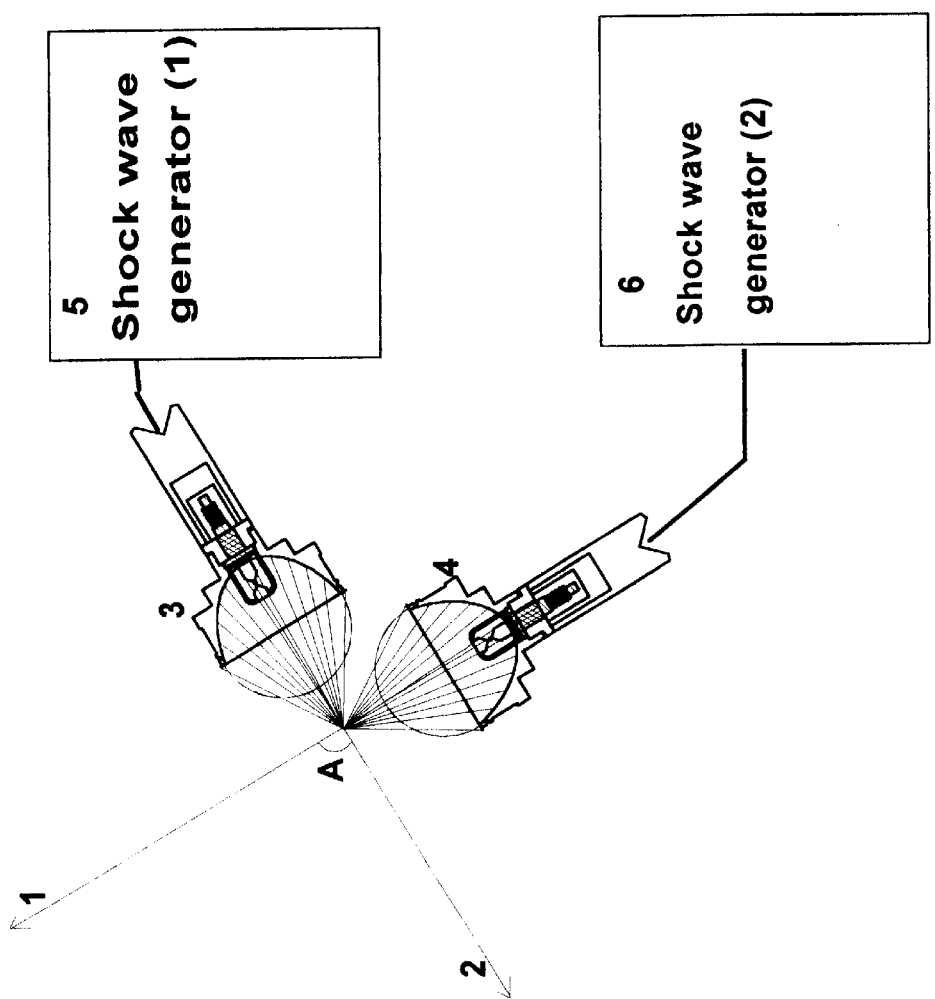
FIG. 2 shows the same configuration where A is the angle between 1 the direction of propagation of shock waves originating from reflector 3 and 2 the direction of propagation of shock waves originating from reflector 4 and where 5 is the first shock wave generator and 6 is the second shock wave generator.
Figure 3:
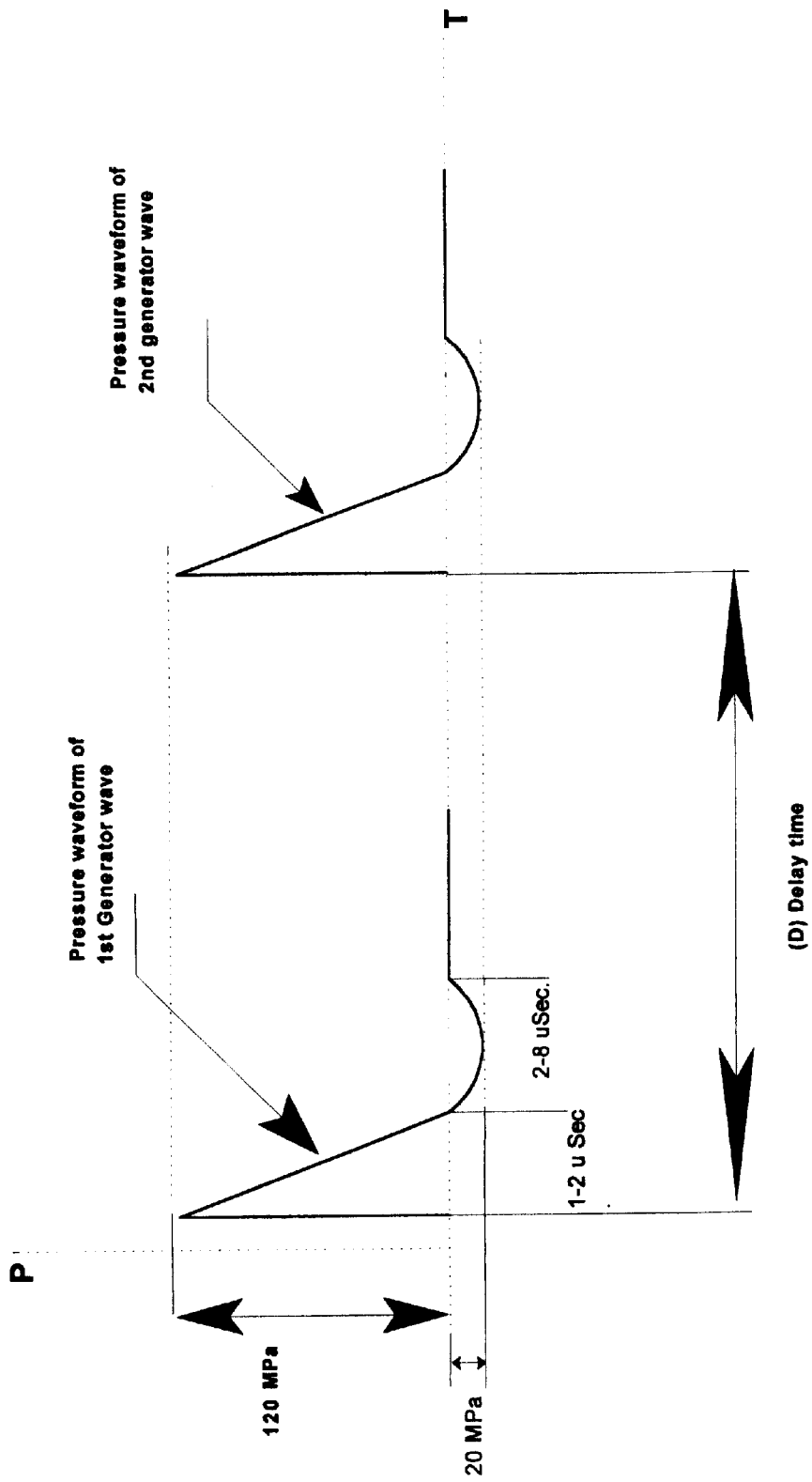
FIG. 3 shows the two shock pulses waveform; one from each of the two shock wave sources and where (D) is the delay time between the two shock waves.

A preferred embodiment of the present invention comprises the usage of two shock wave sources where said shock waves are reaching a focal area each from a different angle and the site where treatment is intended is mobilized to be in the focal area. The angle between the two shock waves is variable, for example from about 67 degrees up to about 105 degrees according to the type of treatment and energy level. However, in a most preferred embodiment this angle is set at about 90 degrees, i.e. the direction of the propagation of the two shock waves are almost perpendicular to each other.

Also, the timing of the generation of the two shock waves is variable from instantaneous generation to a delay period between the two shock waves up to about 100 milliseconds. Yet in the most preferred embodiment, this delay time is set at about 23 milliseconds. Also, according to other embodiments of the invention more than two sources of shock waves may be involved regardless of the selected angles of directions of generated shock waves and/or timing of their generation.

It is obvious to those skilled in the art that many modifications and or alterations may be mode within the description of this invention. Any prior art shock wave generator and reflector may be used in the present invention. In a preferred embodiment, Twinheads™, which was using two shock wave generators, has provided good results on experimental testing on in vitro stones. With an angle between axes of the two reflectors about 90 degrees and delay time of firing between the two sources about 23 micro seconds, the shock wave effects became more concentrated in the focal area with disappearance of any effects outside this focal area.

It was found that stone disintegration was limited to the focal area without propagation outside the F2. Thus, with Twinheads™, damage to the surrounding tissues will be avoided or reduced because of the localization of shock wave effects in the localized focal area. Moreover, the quality of disintegration of stone was finer and more rapid, as it was the result of applying pressure and tension from two different directions to the stone, which enhanced the initiation of cracks and their extension throughout the stone.

We claim:

1. In a shock wave method for fragmenting stones or concretions in a living body or tissue wherein at least two shock wave generators are arranged in cooperative relation to each other such that timed sequential shock wave pulses from said shock wave generators are focused to a focal point at said stones or concretions on or inside the living body or tissue, the improvement comprising controlling the collapse of cavitation bubbles produced by said shock wave pulses by controlling the timing and direction of propagation of each timed shock wave pulse so as to avoid damage to adjacent tissue wherein the directions of propagation between said shock wave pulses has an angle between from about 67° to 105° and wherein said shock wave pulses are generated with a delay time between the two shock wave pulses under about 100 milliseconds.

2. The method defined in claim 1 wherein said angle is about 90°.

3. The method defined in claim 1 wherein said delay time is about 23 milliseconds.

4. The method defined in claim 2 wherein said delay time is about 23 milliseconds.

5. In a shock wave method for fragmenting stones or concretions in a living body or tissue wherein two shock wave generators are arranged in cooperative relation to each other such that timed sequential shock wave pulses from said shock wave generators are focused to a focal point at said stones or concretions on or inside the living body or tissue, the improvement comprising controlling the collapse of cavitation bubbles produced by said shock wave pulses by controlling the timing and direction of propagation of each timed shock wave pulse so as to avoid damage to adjacent tissue wherein the directions of propagation between said shock wave pulses has a fixed angle of about 90° and wherein said shock wave pulses are generated with a delay time between the two shock wave pulses under about 100 milliseconds.

6. In a shock wave method for fragmenting stones or concretions in a living body or tissue wherein two shock wave generators are arranged in cooperative relation to each other such that timed sequential shock wave pulses from said shock wave generators are focused to a focal point at said stones or concretions on or inside the living body or tissue, the improvement comprising controlling the collapse of cavitation bubbles produced by said shock wave pulses by controlling the timing and direction of propagation of each timed shock wave pulse so as to avoid damage to adjacent tissue wherein the directions of propagation between said shock wave pulses has a fixed angle of about 90° and wherein said shock wave pulses are generated with a delay time between the two shock wave pulses of about 23 milliseconds.

* * * * *